(12) United States Patent
Asimacopoulos

(10) Patent No.: US 6,238,431 B1
(45) Date of Patent: May 29, 2001

(54) EXTRACTABLE VARIABLY CONTROLLED DIAMETER STENT AND METHOD OF USING THE SAME

(76) Inventor: Pannayiotis J. Asimacopoulos, 6734 Vanderbilt, Houston, TX (US) 77005

( * ) Notice: Subject to any disclaimer, the term of this patent is extended or adjusted under 35 U.S.C. 154(b) by 855 days.

(21) Appl. No.: 08/794,530

(22) Filed: Feb. 3, 1997

Related U.S. Application Data

(63) Continuation of application No. 08/302,101, filed on Sep. 7, 1994, which is a continuation of application No. 07/969,510, filed on Oct. 30, 1992, now abandoned, which is a continuation of application No. 07/491,356, filed on Mar. 9, 1990, now abandoned.

(51) Int. Cl.$^7$ ........................................................ A61F 2/06
(52) U.S. Cl. .......................................... 623/1.15; 623/1.11
(58) Field of Search .................................... 606/198, 191, 606/194, 108; 604/104; 623/1.15, 1.11

(56) References Cited

U.S. PATENT DOCUMENTS

| | | | |
|---|---|---|---|
| 3,789,852 | * | 2/1974 | Kim et al. ........................ 606/198 X |
| 4,572,186 | * | 2/1986 | Gould et al. ........................ 606/194 |
| 4,740,207 | * | 4/1988 | Kreamer ........................ 606/108 X |
| 4,776,337 | * | 10/1988 | Palmaz ........................ 606/108 |
| 4,877,030 | * | 10/1989 | Beck et al. ........................ 606/195 |
| 4,921,484 | * | 5/1990 | Hillstead ........................ 606/194 X |
| 4,990,151 | * | 2/1991 | Wallsten ........................ 606/108 |
| 4,998,539 | * | 3/1991 | Delsanti ........................ 606/198 X |
| 5,007,926 | * | 4/1991 | Derbyshire ........................ 606/191 X |
| 5,019,090 | * | 5/1991 | Pinchuk ........................ 606/108 X |
| 5,026,377 | * | 6/1991 | Burton et al. ........................ 606/108 |
| 5,037,427 | * | 8/1991 | Harada et al. ........................ 606/108 |
| 5,059,211 | * | 10/1991 | Stack et al. ........................ 606/198 |
| 5,266,073 | * | 11/1993 | Wall ........................ 606/195 X |

OTHER PUBLICATIONS

Sigwart, U., "The Self–Expanding Mesh Stent," *Textbook of Interventional Cardiology*, Ch. 29, pp. 605–622 (W. B. Saunders Co., 1990).

Ellis, S.G., "The Palmaz–Schatz Stent: Potential Coronary Applications," *Textbook of Interventional Cardiology*, Ch. 30, pp. 623–632, (W. B. Saunders Co., 1990).

Roubin, G. S. and K. A. Robinson, "The Gianturco–Roubin Stent," *Textbook of Interventional Cardiology*, Ch. 31, pp. 633–646. (W. B. Saunders Co., 1990).

Slepian, M. J., "Polymetric Endoluminal Paving and Sealing. Therapeutics at the Crossroad of Biomechanics and Pharmacology," Textbook of Interventional Cardiology, Ch. 32, pp. 647–670.

* cited by examiner

*Primary Examiner*—Michael H. Thaler

(57) ABSTRACT

An extractable stent which has a tubular housing with a variably controlled diameter. The housing includes first and second arms; a balloon or other removable carrier with a variably controlled diameter, in the preferred embodiment, for expanding and reducing the variably controlled diameter of the housing; and co-acting stopshoulders along or adjacent to the longitudinal edges of the first and second arms, in the preferred embodiment, for releasably holding the housing in at least one expanded diameter.

9 Claims, 2 Drawing Sheets

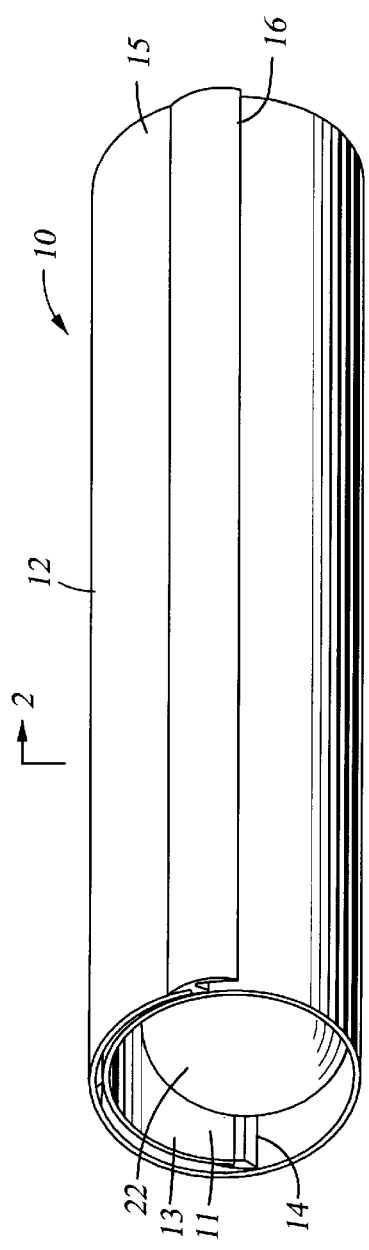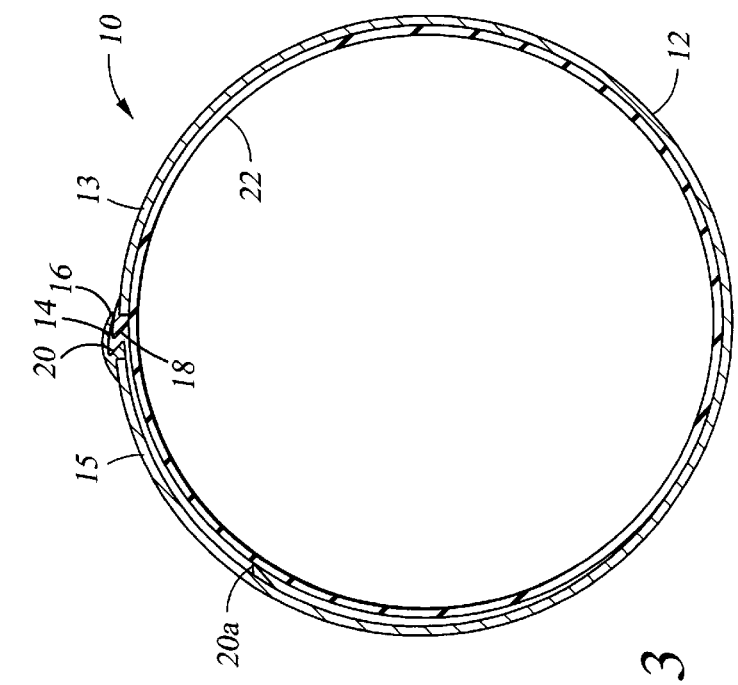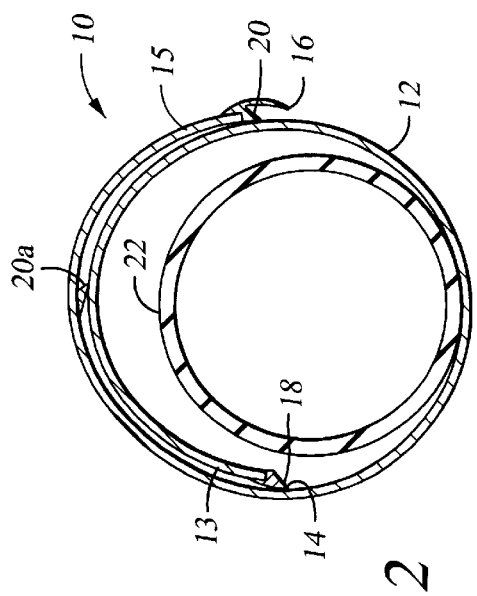

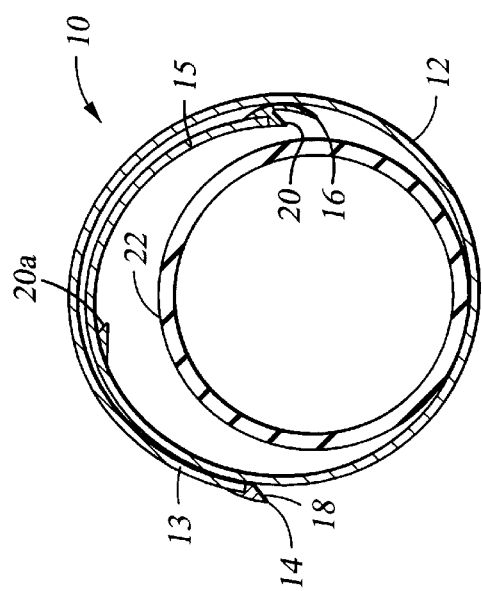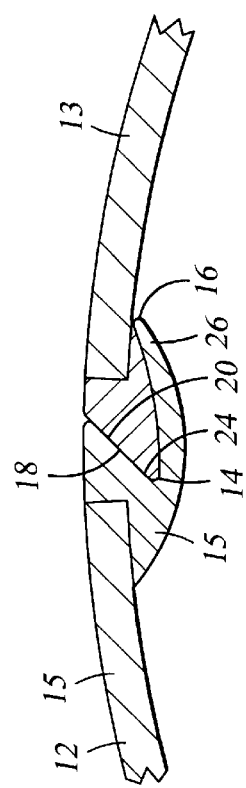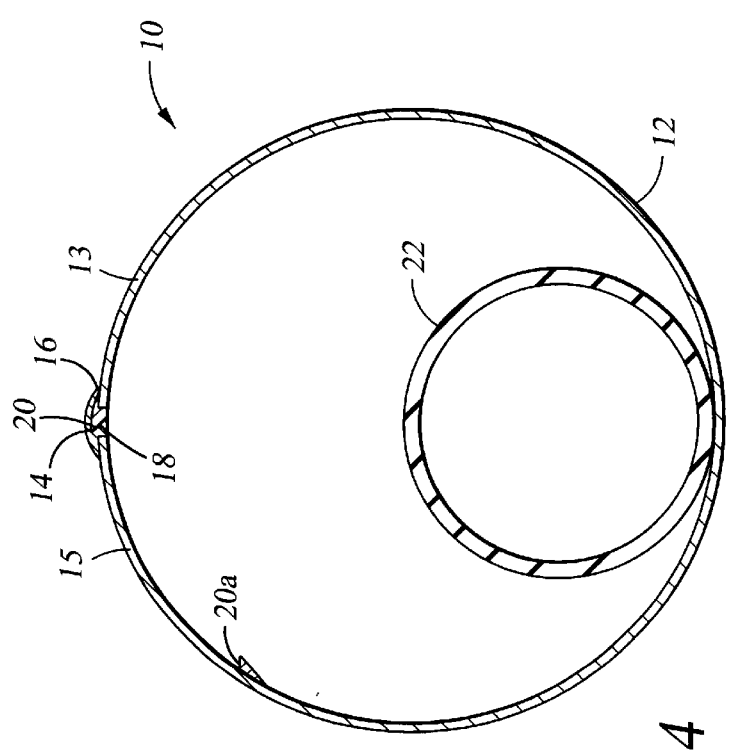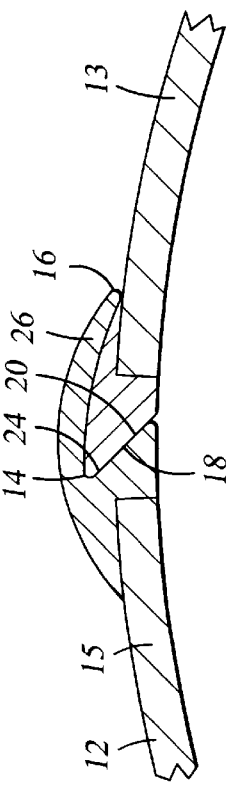
Fig. 6
Fig. 7
Fig. 4
Fig. 5

EXTRACTABLE VARIABLY CONTROLLED DIAMETER STENT AND METHOD OF USING THE SAME

This application is a continuation of copending application(s) Ser. No. 08/302,101 filed on Sep. 7, 1994 which was a continuation of prior copending application Ser. No. 07/969,510 filed on Oct. 30, 1992 now abandoned, which was a continuation of prior copending application Ser. No. 07/491,356 filed on Mar. 9, 1990, now abandoned.

BACKGROUND OF THE INVENTION

This invention generally relates to a stent, and more particularly, to a device for insertion in the lumen of hollow organs and tubular parts of the bodies of animals, including humans, for supporting and holding open the organs or body parts such as blood vessels, trachea, ureter, esophagus, viscera or any tubular or hollow organs during treatment of diseases. The stent includes a longitudinal passageway for conveying fluids and solids through the lumen of body parts.

Stents have been known and used in the past. Although the diameter of conventional stents is expandable in order to be fixed in place and to maintain dialation, they cannot be removed. The problem with conventional stents is that they can be changed in diameter to fit a particular hollow organ or body part and anchored in place, but once this is done, they cannot be reduced in size and removed.

Some conventional stents are helixes or springs that can be compressed parietally of transversely and may change in diameter. Solids can possibly become lodged between the coils of the stent. This will block the flow of fluids through the organ or tubular body part. Also, the body can build up fibrous tissues, neointima, fiberous tissue or plaque around or inside the coils of the stent. When this happens, the stent becomes embedded in the body tissues and is difficult or impossible to remove.

In conventional stents designed with rough surfaces (gaps and holes such as netting or helixes), the body can build up fibrous tissue or neointima on the rough surface, obstruct or occlude the movement of solids or fluids through the body part thus preventing extraction of the stent. Secondarily, solids passing through the body part could become embedded in the rough surface of the stent and obstruct movement of material through the body part. Conventional stents, therefore, usually are not removed, but become permanently implanted.

SUMMARY OF THE INVENTION

It is therefore an object of the invention to provide a stent that can be inserted to the desired destination, expanded to the desired size, locked in place for a designated period of time, unlocked, contracted in size and then removed.

Another object of the invention is to provide a stent that can be serially dialated and releasably locked in different stages by expanding the diameter.

Still another object of the invention is to provide a stent that can be inserted percutaneously or through a native orifice at any diameter that is smaller than is needed to support or fit a hollow or tubular body part at the target point.

According to the present invention the improved stent includes a resilient, tubular housing for supporting hollow organs or tubular body parts, said tubular housing including a longitudinal passageway for conveying fluids or solids through said organs or said parts; a variably controlled diameter; a means for expanding the variably controlled diameter; and a means for releasably holding at least one expanded diameter.

BRIEF DESCRIPTION OF THE DRAWINGS

The features of this invention which are believed to be novel are set forth with particularity in the appended claims. The invention itself, however, together with its objects and the advantages thereof., will be best understood by reference to the following description taken in connection with the accompanying drawings, in which:

FIG. 1 is a perspective elevational view of the stent in insertable and non-expanded position with a deflated actuating balloon therein;

FIG. 2 is a cross section through the stent taken along line 2—2 of FIG. 1;

FIG. 3 is a similar view as FIG. 2 which shows the balloon inflated and the stent in an expanded position;

FIG. 4 is a similar view as FIG. 3 which shows the stent in a locked position and the balloon removed;

FIG. 5 is an enlarged elevational view, in cross section, of the releasable locking means at the first and second longitudinal edges in the locked position holding the stent in an expanded position;

FIG. 6 is a cross section view of the configuration of the stent in a released position ready to be extracted; and FIG. 7 is an elevational view, in cross section, of an alternate configuration of the releasable locking means at the first and second longitudinal edges in the locked position.

DESCRIPTION OF THE PREFERRED EMBODIMENT

Referring now to the drawings, and particularly FIG. 1, the stent 10 includes a cylindrical housing 12 having first and second arms 13 and 15 with first and second longitudinal edges 14 and 16, respectively, and a longitudinal passageway 11 therethrough. Preferably the stent 10 is manufactured from any one of a variety of resilient, elastic, non-toxic, non-thrombogenic relatively inert materials such as stainless steel, teflon or materials used for synthetic cardiac valves and similar prosthetic devices which are naturally or can be made radiopaque through the use of radiopaque markers. More preferably the housing is formed from tantalum. The stent 10 is inserted into the lumen of a hollow organ or tubular body part of an animal, including a human, percutaneously or through a native orifice using standard insertion techniques.

The housing 12 has a variably controlled diameter such as not less than 0.5 millimeters. Therefore, the stent 10 includes a means for expanding the stent's diameter to a locking position and a means for reducing the stent's diameter to no less than its original diameter. In the preferred embodiment, the means for expanding and reducing the variably controlled diameter is a removable balloon 22 or other carrier with a variably controlled diameter. Most preferably, the balloon 22 is of the type used in angioplasty. The housing 12 includes a means for holding said body in at least one expanded diameter. Preferably this holding means is a means for releasably locking the housing 12. In the preferred embodiment, the releasably locking means includes co-acting stopshoulders 18 and 20. The stopshoulders 18 and 20 are preferably positioned along the longitudinal edges 14 and 16 of the housing 12. The stopshoulders 18 and 20 include flanges of a discrete length and preferably the same length as the first and second longitudinal edges and 16 or a series of spaced shoulders interspersed along the longitudinal edges 14 and 16. If desired, additional stopshoulders 20a are positioned adjacent to the second longitudinal edge 16 on the interior of the housing 12 and spaced from stopshoulder 20 to enable locking the stent in place at more than one expanded diameter (FIGS. 2 and 3).

The first and second arms 13 and 15 of the stent 10 are resiliently and radially biased inwardly so that they have the same radius from the center line of the longitudinal passageway 11 of the housing 12. The resilient bias characteristics of the first and second arms 13 and 15 helps to minimize the stent's diameter in the insertable position (FIGS. 1 and 2) and in a released position (FIG. 6). The bias characteristics also facilitate locking the stent (FIG. 4).

As shown in FIGS. 1 and 2, the balloon 22 or other carrier with a variably controlled diameter is inserted in the longitudinal passageway 11. Then the balloon 22 is inflated and expands the diameter of the housing 12 (see FIGS. 2 and 3). The balloon 22 is inflated to a point where the co-acting stopshoulders 18 and 20 have passed each other but the first and second longitudinal edges 14 and 16 remain overlapping (FIG. 3). The balloon 22 then is slightly deflated so that the co-acting stopshoulders 18 and 20 engage or lock. (FIGS. 4 and 5) Stopshoulder 18 fits with a recess 24 in stopshoulder 20 and is prevented from prematurely releasing by an external lip 26 on stopshoulder 20. (FIG. 5) Once the co-acting stopshoulders 18 and 20 are engaged or locked, the balloon can be further deflated and removed percutaneously or through a native orifice using standard removal techniques.

After the stent has been in place a sufficient amount of time, the stent 10 can be removed. First, a balloon 22 or other carrier with a variably controlled diameter is re-inserted in the longitudinal passageway 11 of the housing 12. Second, the balloon 22 is inflated to expand the stent's diameter beyond the point where the first and second longitudinal edges 14 and 16 do not overlap and are separated. Then the balloon 22 is deflated. When the balloon 22 is deflated, the curved shaped of the external lip 26 on stopshoulder 20 in combination with bias characteristics of the first and second arms 13 and 15 cause the first longitudinal edge 14 to pass over the top of the second longitudinal edge 16 in a manner preventing the co-acting stopshoulders 18 and 20 from re-engaging or locking. That is, longitudinal edge 14 slides along and against the outside of the external lip 26, longitudinal edge 16 and arm 15 of the tubular bod 12 reducing the stent's diameter and assuming the least configuration shown in FIG. 6. The entire stent 10 including balloon 22 or other carrier then can be removed percutaneously or through a native orifice using standard removal techniques.

Although FIGS. 1–6 show the invention in its preferred embodiment, alternative designs can include other configurations. For example, in one alternative design, the orientation of the first and second longitudinal edges 14 and 16 is reversed so that the configuration in FIG. 6 is the configuration of the stent in its non-expanded position before it is inserted into the lumen and configuration in FIG. 2 is the configuration of the stent in its released position before it is removed. This design requires re-orienting stopshoulder 20, recess 24 and external lip 26 as shown in FIG. 7. In still other designs, the orientation of the longitudinal edges 14 and 16 in their contracted and released positions are the same; e.g., they may start out as in FIG. 2 at the stent's insertion and return to the configuration in FIG. 2 after the stent is unlocked before it is removed.

The novel features and characteristics of this invention are set forth in the appended claims. While the invention is susceptible to various modifications and alternative constructions, a certain illustrated embodiment thereof has been shown in the drawings and described above in detail. Various changes and modifications to the preferred embodiments described herein will be apparent to those skilled in the art; for example, using a horizontally or circumferentially telescoping probe or a screw or rachet device as a means for expanding or reducing the diameter of the stent or substituting a co-acting ridge and groove combination for co-acting shoulderstops. It should be understood, however, there is no intention to limit the invention to the specific form disclosed, but on the contrary, the intention is to cover all modifications, alternative constructions and equivalents falling within the spirit and scope of the invention.

What is claimed is:

1. A stent assembly for insertion in the lumen of hollow organs and tubular parts of the body comprising:

a resilient, cylindrical housing for supporting hollow organs or tubular parts, said housing including a longitudinal passageway for conveying fluids and solids through said organs or said parts;

said housing having a variably controlled diameter and first and second arms forming first and second longitudinal edges, respectively, of said housing, said first and second longitudinal edges being biased radially inwardly toward a reduced diameter for said housing, one of said first and second longitudinal edges of said first and second arms overlapping the other of said longitudinal edges when said housing is in a reduced diameter state;

means for expanding said variably controlled diameter;

first locking means disposed on or adjacent to one of said first and second longitudinal edges and engageable with second locking means disposed on or adjacent to the other of said first and second longitudinal edges for releasably, lockingly holding said housing in at least one expanded diameter when said housing is expanded to a first predetermined housing diameter less than that required for separation of said overlapping longitudinal edges, and when said means for expanding said variably controlled diameter is deactivated, said arms actuating radially inwardly according to said bias to assume for said housing said at least one expanded diameter; and said first and second arms of said housing further comprising shaped profile means forming a part of said first and second locking means for positively causing said first and second locking means to slide over one another and for positively preventing reengagement thereof, for positively releasing said first locking means from said second locking means upon actuation of said means for expanding said variably controlled diameter to a second predetermined housing diameter effecting separation of said overlapping longitudinal edges and subsequent deactivation of said means for expanding said variably controlled diameter, said biased edges reducing said variably controlled diameter of said housing to a smaller diameter.

2. The stent assembly recited in claim 1, further including means for reducing said variably controlled diameter, and wherein said means for expanding said variably controlled diameter and said means for reducing said variably controlled diameter are the same.

3. The stent assembly recited in claim 2, wherein said means for expanding and reducing said variably controlled diameter is a removable carrier with a variably controlled diameter.

4. The stent assembly recited in claim 3, wherein said carrier is a balloon.

5. The stent assembly recited in claim 3, wherein said locking means includes co-acting stopshoulders positioned on said first and second longitudinal edges.

6. The stent assembly recited in claim 3, wherein said locking means includes a pair of co-acting stopshoulders, one of said stopshoulders being positioned adjacent to one of said first and second longitudinal edges, and the other of said stopshoulders being positioned at the other of said first and second longitudinal edges.

7. A method for supporting hollow organs or tubular parts of the body comprising:

inserting in the lumen of hollow organs or tubular parts a resilient, cylindrical housing having a variably controlled diameter and first and second arms forming longitudinal edges of said housing, said longitudinal edges being biased radially inwardly toward a reduced diameter for said housing, one of said longitudinal edges overlapping the other of said longitudinal edges when said housing is in a reduced diameter state, said housing including a longitudinal passageway for conveying fluids and solids through said organs or said parts;

expanding said variably controlled diameter to a first predetermined housing diameter less than that required for separation of said overlapping longitudinal edges;

reducing said variably controlled diameter and inserting a first locking means disposed on or near the edge of one of said arms into a second locking means disposed on or near the edge of the other of said arms for releasably, lockingly holding said housing in at least one expanded diameter for an appropriate period of time; and later expanding said variably controlled diameter to a second predetermined housing diameter effecting separation of said overlapping longitudinal edges, followed by reducing said variably controlled diameter and positively causing said first locking means to slide over said second locking means to positively prevent reengagement thereof, thereby positively releasing said first locking means from said second locking means and reducing said variably controlled diameter for removal.

8. The method of claim 7, wherein said steps of expanding and reducing said variably controlled diameter are done by expanding and reducing a removable carrier with a variably controlled diameter.

9. The method of claim 8, wherein said carrier is a balloon.

* * * * *